(12) United States Patent
Kawabata

(10) Patent No.: US 8,003,366 B2
(45) Date of Patent: Aug. 23, 2011

(54) BACILLUS BACTERIUM STRAIN CAPABLE OF DECOMPOSING/VOLUME-REDUCING PLANT RESIDUE

(75) Inventor: Takahiro Kawabata, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 234 days.

(21) Appl. No.: 12/439,606

(22) PCT Filed: Sep. 21, 2007

(86) PCT No.: PCT/JP2007/068353
§ 371 (c)(1),
(2), (4) Date: Mar. 2, 2009

(87) PCT Pub. No.: WO2008/041505
PCT Pub. Date: Apr. 10, 2008

(65) Prior Publication Data
US 2010/0028974 A1    Feb. 4, 2010

(30) Foreign Application Priority Data
Oct. 4, 2006  (JP) ................................. 2006-273131

(51) Int. Cl.
*C12N 1/20* (2006.01)
*C12N 1/00* (2006.01)
*C12S 3/00* (2006.01)
*A01N 63/00* (2006.01)

(52) U.S. Cl. ............... 435/252.31; 435/252.1; 435/262; 435/267; 435/274; 435/275; 435/277; 435/832; 424/93.46

(58) Field of Classification Search ......................... None
See application file for complete search history.

(56) References Cited

U.S. PATENT DOCUMENTS
6,165,775 A    12/2000  Shigemitsu

FOREIGN PATENT DOCUMENTS
| JP | 10 304773 | 11/1998 |
| JP | 11 225748 | 8/1999 |
| JP | 3283228 | 3/2002 |
| JP | 2005 130737 | 5/2005 |

OTHER PUBLICATIONS

Shimizu et al., "Sacchi Bunkai Saikin no Bunri to Baiyo Seiriteki Seishitsu, 2000", Journal of Japanese Society of Turfgrass Science, vol. 29, No. 1, pp. 22 to 31, 27, table 4, (2000).

L. Link, et al., "Extreme Spore UV Resistance of *Bacillus pumilus* Isolates Obtained from an Ultraclean Spacecraft Assembly Facility", Microbial Ecology, XP-002600583, vol. 47, No. 2, 2004, pp. 159-163.

*Primary Examiner* — Vera Afremova
(74) *Attorney, Agent, or Firm* — Oblon, Spivak, McClelland, Maier & Neustadt, L.L.P.

(57) ABSTRACT

Disclosed is a method for decomposing a plant residue and reducing a volume of the plant residue to a satisfactory level within a short period. Also disclosed is a bacterium for use in the method. Further disclosed is a material for decomposing a plant residue and reducing a volume of the plant residue, which contains the bacterium. A bacterium is found which is capable of decomposing a plant residue and reducing a volume of the plant residue under natural conditions satisfactorily and stably. The bacterium can be used for decomposing a plant residue and reducing a volume of the plant residue. A material containing cells of *Bacillus pumilus* KS-C4 strain (FERM BP-10842) that is capable of decomposing a plant residue and reducing a volume of the plant residue or a culture of the cell is added to a plant residue.

7 Claims, No Drawings

SEQUENCE LISTING

```
<160> NUMBER OF SEQ ID NOS: 1

<210> SEQ ID NO 1
<211> LENGTH: 532
<212> TYPE: DNA
<213> ORGANISM: Bacillus pumilus

<400> SEQUENCE: 1
gagtttgatc ctggctcagg acgaacgctg gcggcgtgcc taatacatgc aagtcgagcg     60
aacagaaggg agcttgctcc cggatgttag cggcggacgg gtgagtaaca cgtgggtaac    120
ctgcctgtaa gactgggata actccgggaa accggagcta ataccggata gttccttgaa    180
ccgcatggtt caaggatgaa agacggtttc ggctgtcact tacagatgga cccgcggcgc    240
attagctagt tggtgggta atggctcacc aaggcgacga tgcgtagccg acctgagagg    300
gtgatcggcc acactgggac tgagacacgg cccagactcc tacgggaggc agcagtaggg    360
aatcttccgc aatggacgaa agtctgacgg agcaacgccg cgtgagtgat gaaggttttc    420
ggatcgtaaa gctctgttgt tagggaagaa caagtgcgag agtaactgct cgcaccttga    480
cggtacctaa ccagaaagcc acggctaact acgtgccagc agccgcggta at            532
```

BACILLUS BACTERIUM STRAIN CAPABLE OF DECOMPOSING/VOLUME-REDUCING PLANT RESIDUE

CROSS-REFERENCE TO RELATED APPLICATIONS

The present application is a 35 U.S.C. §371 National Stage patent application of International patent application PCT/JP2007/068353, filed on Sep. 21, 2007, which claims priority to Japanese patent application JP 2006-273131, filed on Oct. 4, 2006.

TECHNICAL FIELD

The present invention relates to a novel *bacillus* strain capable of decomposing a plant residue and reducing a volume of the plant residue, a material for decomposing a plant residue and reducing a volume of the plant residue which includes the novel *bacillus* bacterium strain, and a method of decomposing a plant residue and reducing a volume of the plant residue by using the *bacillus* bacterium strain and the material.

BACKGROUND ART

In gardens and the greens of golf courses, it is necessary to trim the turf periodically, and therefore, mowed residues of the grass are generated periodically. Further, the mowed residues, grass, and stems, leaves, and roots of other plants, which are dead, accumulate on the lawn grass without decomposing, and a thatch is formed. It is known that, if the mowed turf or thatch thus generated is left for a long time period, various kinds of pathogenic bacteria are generated and proliferated and a toxic gas is generated, with the result that damages such as death and failure in growing of the turf occur. In particular, if pathogenic fungi which form spores are once generated, the forming of the spores proceed in the thatch layer to be a new inoculation source for the pathogenic fungi, resulting in more serious damages. In addition, it is known that the accumulation of the mowed turf or the thatch layer with a certain thickness on the soil prevent air, water, a nutrient source, and an agricultural chemical from transferring to the soil or the root of the turf, with the result that growing of the turf is inhibited and a disease is apt to develop. Conventionally, in order to remove the mowed turf or the thatch causing the problems, vertical and aeration are performed or physical means such as topdressing are used in golf courses and the like. However, it is difficult to say that those methods are easy methods. There have been problems that periodic conduction thereof needs labor and those methods cost much. In addition, the mowed turf and the thatch could not be removed sufficiently by those methods.

In addition, weeds grown at the river location or on roads have been administered by mowing down, drying, collecting, exporting, or burning of weeds. At present, easy broadcast burning and landfill dispositions are strictly regulated by laws. In particular, dispositions of a large amount of mowed grass leads to big problems in view of the environment, beauty, and cost.

In addition, the residue remained after harvest of crops becomes a source of the pathogenic fungi when left to stand as it is in the field, and hence, rapid removal or decomposition thereof is desired. However, there are big problems in the environment and cost as well as the above-mentioned administration of weeds.

Under such circumstances, a method of removing mowed turf or thatch by decomposition and volume reduction with a microorganism such as a bacterium is proposed. For example, there are known bacteria belonging to *Penicillium* and *Bacillus macerans*, which are capable of degrading cellulose. In addition, there is proposed an application of the bacteria to the soil containing a mowed turf or a thatch layer (Patent Documents 1 and 2). However, a microorganism material containing the bacteria does not have the ability of decomposing the mowed turf or the thatch sufficiently, thereby being not practical. Further, any one of the above bacteria proliferates and decomposes the mowed turf or the thatch in a predetermined test condition, but in the practical use, the natural conditions such as sunshine, temperature, and rainfall influence largely on the proliferation rate. Therefore, there have been problems that sufficient and stable effects cannot be obtained.

In addition, a method of using weeds by composting has been studied, but specific microorganism to be applied has not been studied sufficiently, and there is a problem that stable effects cannot be obtained (Patent Document 3).

Patent Document 1: JP 3324979 B
Patent Document 2: JP 3283228 B
Patent Document 3: JP 11-240784 A

DISCLOSURE OF THE INVENTION

A purpose of the present invention is to provide a method of decomposing a plant residue and reducing the volume of the plant residue sufficiently in a short period, a bacterium to be used in the method, and a material including the bacterium for decomposing a plant residue and reducing the volume of the plant residue. In particular, another purpose of the present invention is to find a bacterium having an ability of decomposing a plant residue and reducing the volume of the plant residue sufficiently and stably even under natural conditions and to use the bacterium for decomposing the plant residue and reducing the volume of the plant residue.

The inventors of the present invention have extensively studied in order to achieve the above-mentioned purposes, with the result that the inventors have found a bacterium excellent in an ability of decomposing a plant residue and reducing the volume of the plant residue. Then, the inventors added a material containing a culture obtained by culturing the bacterium to a plant residue, and found that decomposition and volume reduction of the plant residue was proceeded, thereby completing the present invention.

That is, the present invention provides:

(1) a *Bacillus pumilus* KS-C4 strain (FERM BP-10842) having an ability of decomposing a plant residue and reducing a volume of the plant residue;

(2) a material for decomposing a plant residue and reducing a volume of the plant residue, containing, as an active ingredient, cells of the strain according to the item (1) and/or a variant of the strain having an ability of decomposing a plant residue and reducing a volume of the plant residue, or a culture of the cells; and (3) a method of decomposing a plant residue and reducing a volume of the plant residue, including adding the material for decomposing a plant residue and reducing a volume of the plant residue according to the item (2) to a plant residue.

BEST MODE FOR CARRYING OUT THE INVENTION

The *Bacillus pumilus* KS-C4 strain of the present invention is a strain isolated from the soil in a golf course in Saitama by the inventors of the present invention and is characterized by having an ability of decomposing a plant residue and reducing the volume of the plant residue. The term "plant residue" refers to a substance containing at least part of a plant body such as a leaf, a stem, a flower, or a root of a plant, and requiring removal and decomposition thereof. Examples of the plant residue include wood substances such as a mowed turf or a thatch in a golf course or a garden, a sawdust, a bark, and a pruned material, straws such as a rice straw and wheat straw, crop residues such as a chaff and a bran, harvest residues of crops and the like, root residues of crops in the soil, domestic raw refuse including plants such as vegetables, feces of livestock ingesting plants, and food industrial wastes. In addition, the term "ability of decomposing and volume reducing" refers to an ability of decreasing the mass or volume of the solid content of the plant residue as a result of the fact that, when bacterium cells are added to a pant residue, the bacterium proliferates using, as nutrient sources, polysaccharides constituting a plant body included in the plant residue.

The mycological properties of the *Bacillus pumilus* KS-C4 strain are as follows.

The KS-C4 strain has a cellulase activity and a pectinase activity. The phrase "has a cellulase activity and a pectinase activity" refers to producing those enzymes to such an extent that the cellulase activity and the pectinase activity can be detected in a culture obtained by culturing the cells. Specifically, the phrase refers to the following: cellulase and pectinase are produced inside the cells; and the produced cellulase and the produced pectinase are adhered to an outside of the cell walls or the produced cellulase and the produced pectinase are secreted outside the cells.

The cellulase is an enzyme hydrolyzing β1→4 glucoside bond of the cellulose. The cellulase includes both endoglucanase, which degrades cellulose chains randomly, and cellobiohydrolase, which degrades the cellulose chains from a reducing terminal of the cellulose and produces cellobiose. The pectinase is an enzyme which hydrolyze α1→4 bond of galacturonic acid constituting pectin, pectinic acid, and pectic acid.

The DNA base sequence of a 16S rRNA gene of the KS-C4 strain is shown in SEQ ID NO: 1. In addition, as a result of a homology search of the gene shown in GenBank/DDBJ/EMBL by using BLAST, the 16S rRNA gene of the KS-C4 strain showed high homology, i.e. 99.8% homology, with a 16S rRNA of *Bacillus pumilus* DSMZ 27.

From the foregoing, the KS-C4 strain was supposed to belong to *Bacillus pumilus*.

The KS-C4 strain has been deposited to International Patent Organism Depositary of Advanced Industrial Science and Technology (central 6, 1-1-1 Higashi Tsukuba, Ibaraki) with accession No. FERM P-20978 as of Aug. 2, 2006. Then, the strain was transferred to the international deposition under Budapest Treaty and assigned with accession No. FERM BP-10842 on Jun. 19, 2007.

The KS-C4 strain can be cultured by a conventional method used in culturing *Bacillus pumilus*. For example, the strain can be cultured at a temperature of 10 to 40° C., and in general, cultured at a temperature of preferably 30 to 35° C. In addition, as the culture method, a liquid culture method by a reciprocating shake culture or a jar fermentor culture or a solid culture method can be used.

The medium component used in the culture is also not particularly limited. Any one of animal and plant media can be used, and for example, a material containing a bran, a rice bran, a wheat, a daily product, or the like can be used. Further, as carbon sources, saccharides such as glucose, sucrose, and molasses, organic acids such as citric acid, and alcohols such as glycerin may be added and, as nitrogen sources, ammonium salts and nitrates such as ammonia, ammonium sulfate, ammonium chloride, and ammonium nitrate may be added.

In addition, in order to store the cells of the KS-C4 strain, the strain is preferably stored by forming the cells in a state of spores and drying the spores from the viewpoint of quality stability. In the case of forming the spores, in the culture cycle, culture conditions such as the composition of the medium, pH of the medium, culture temperature, culture humidity, oxygen concentration upon the culture may be adjusted so as to be suitable for spore-forming conditions.

The material for decomposing a plant residue and reducing the volume of the plant residue of the present invention is characterized by containing, as an active ingredient, cells of the KS-C4 strain and/or a variant of the KS-C4 strain having an ability of decomposing a plant residue and reducing the volume of the plant residue, or a culture of the cells. The term "culture of the cells" refers to a culture obtained by culturing the cells.

As the variant and the recombinant strain of the KS-C4 strain used in the present invention, a strain having an ability of decomposing a plant residue and reducing the volume of the plant residue and maintaining the ability can be used.

The variant of the KS-C4 strain can be obtained by the following: the KS-C4 strain mutate naturally or the strain is subjected to a mutation treatment with a chemical mutating agent or ultraviolet rays; and a strain having equal or enhanced ability of decomposing a plant residue and reducing the volume of the plant residue compared to the KS-C4 strain is selected. In addition, it is preferred to select a strain maintaining other favorable properties.

In addition, in the present invention, the recombinant strain of the KS-C4 strain can be used. The recombinant strain can be obtained by the following, for example: a gene regulating an expression of a gene involved in an ability of decomposing a plant residue and reducing the volume of the plant residue is modified to enhance the expression of the gene; and the gene is introduced into the KS-C4 strain. In addition, a gene may be modified so as to enhance or provide other favorable properties other than the above ability.

In the description of the present invention, the variant of the KS-C4 strain may be collectively referred to as "KS-C4 strain" simply.

The KS-C4 strain included in the material for decomposing a plant residue and reducing the volume of the plant residue of the present invention may be in a state of spores or in a state of nurse cells. In general, the strain is preferably in a state of spores from the viewpoint of storage stability.

The cell concentration of the KS-C4 strain in the material for decomposing a plant residue and reducing the volume of the plant residue of the present invention is not particularly limited as long as the cells are not killed in adding the cells in the plant residue and the cells can proliferate. The cell concentration is preferably $1 \times 10^4$ to $1 \times 10^{11}$ CFU/g and more preferably $1 \times 10^7$ to $1 \times 10^{10}$ CFU/g.

In addition, the material for decomposing a plant residue and reducing the volume of the plant residue of the present invention preferably further includes a nutrient source for proceeding the proliferation of the bacterium belonging to *Bacillus*. The addition of the nutrient source enables rapid decomposition and volume reduction of the plant residue because the proliferation of the bacterium belonging to *Bacillus* is proceeded after the material for decomposing a plant residue and reducing the volume of the plant residue of the present invention is added to the plant residue.

The kind of the nutrient source is not particularly limited as long as the effects of the present invention are not impaired, and in general, a nutrient source used in the proliferation of the bacterium belonging to *Bacillus* may be selected.

The material for decomposing a plant residue and reducing the volume of the plant residue of the present invention can be produced by using at least part of the culture obtained by culturing the KS-C4 strain, which includes cells of the KS-C4 strain, as it is, or by mixing the culture with another arbitrary component.

For example, in the case where the cells are cultured using a solid medium, at least part of the obtained culture is dried and pulverized to thereby be used in the production of the material for decomposing a plant residue and reducing the volume of the plant residue. In addition, in the case where the cells are cultured using a liquid medium, the obtained culture can be used as it is or used after the cells are separated by centrifugal separation of the obtained culture and dried by a spray drying or a freeze drying.

The material for decomposing a plant residue and reducing the volume of the plant residue is preferably dried in order to enhance quality stability and storage stability as a product. The material for decomposing a plant residue and reducing the volume of the plant residue is preferably dried to have a water content of 10 mass % or less. The drying method is not particularly limited and examples thereof include a natural drying, a forced-air drying, a spray drying, and a freeze drying. Of those, the spray drying and the forced-air drying are preferably used. Upon the drying, a protective agent such as skim milk, sodium glutamate, and saccharides can be used. In the case of using the saccharides, glucose or trehalose can be used. Further, after the drying, the obtained dried product is preferably added with a deoxidant or a dehydrating agent, put in an gas-barrier aluminum bag to be sealed, and stored at room temperature to low temperature. Thus, the living bacteria can be stored for a long period.

In addition, the material for decomposing a plant residue and reducing the volume of the plant residue of the present invention may be processed by adding arbitrary substances such as a liquid carrier, a solid carrier, a surfactant (emulsifier, dispersant, anti-foaming agent, and the like), and an adjuvant to cells or cell culture of the KS-C4 strain. Those arbitrary substances are not particularly limited as long as they are safe in view of the environment and a substance generally used in a soil atomizing agent or a fertilizer may be used.

Examples of the liquid carrier include a phosphate buffer, a carbonate buffer, and physiological saline solution. In addition, examples of the solid carrier include natural mineral powders of kaolin, clay, talc, chalk, quartz, palygorskite (attapulgite), montmorillonite, diatom earth, and the like, synthetic mineral powders of silicone oxide, alumina, and silicate, and a polymer natural products such as crystalline cellulose, corn starch, gelatin, and arginic acid. In addition, examples of the surfactant include polyoxyethylene/fatty acid ester, polyoxyethylene/fatty alcohol ester, alkyl aryl polyglycol ether, alkyl sulfonate, alkyl sulfate, and aryl sulfonate. Examples of the adjuvant include carboxymethyl cellulose, polyoxyethyleneglycol, acacia gum, starch, and lactose.

The material for decomposing a plant residue and reducing the volume of the plant residue of the present invention is used by adding the material into the plant residue. As the addition method, an appropriate method can be used according to the place where the plant residue of interest is present and the area of the place. For example, when the material is applied to a plant residue in a golf course, a garden, or an arable land, for example, a method involving spraying a dust formulation or a method involving spraying a dust formulation diluted with a liquid such as water about 1,000-fold are exemplified. In addition, when the material is applied to a raw refuse, a dejection of livestock, a food industrial waste, or the like, a method involving mixing the material after a dust formulation or a liquid formulation is added.

The addition amount of the material for decomposing a plant residue and reducing the volume of the plant residue is not particularly limited as long as the number of the cells is enough for the KS-C4 strain to proliferate without being killed. For example, in terms of dried powder, the material is added at a concentration of generally 0.1 to 50 $g/m^2$ and preferably 0.5 to 10 $g/m^2$, or 0.1 to 100 $g/m^3$ and preferably 0.5 to 20 $g/m^3$.

In addition, the material for decomposing a plant residue and reducing the volume of the plant residue may be used together with an inorganic fertilizer, an organic fertilizer, a herbicide, and the like, which are generally used in breeding of plants.

EXAMPLES

(1) Isolation of KS-C4 Strain

A soil containing a thatch part of a golf course in Saitama was mixed with a mowed grass of *Zoysia tenuifolia Willd* and water, and the whole was left to stand at 25° C. for 30 days. Next, from the soil, 10 strains of *Bacillus* bacteria which formed big hallows (clear zone) in an agar plate containing carboxymethyl cellulose (CMC) were isolated. Of those, a strain having the highest ability of decomposing mowed *Zoysia tenuifolia Willd* turf was selected and named as KS-C4 strain.

(2) Production of Material for Decomposing Plant Residue and Reducing Volume of Plant Residue The KS-C4 strain obtained as described above was cultured in a bouillon medium (a liquid medium containing a meat extract, peptone, $KH_2PO_4$, $MgSO_4$) at 30° C. for 2 days. The obtained liquid culture was used as a material for decomposing a plant residue and reducing the volume of the plant residue of Example 1. The cell concentration of the liquid culture was $1 \times 10^9$ CFU/ml. In addition, a *Bacillus pumilus* NBRC 12092 strain and a *Bacillus subtilis* BSTH-1 strain were similarly cultured and the obtained liquid cultures were used as materials of Comparative Example 1 and Comparative Example 2.

Next, those liquid cultures were each inoculated, as an inoculation source, in round soybeans (sterilized with an autoclave at 121° C. for 30 minutes) as a substrate of a solid culture, and cultured at 30° C. for 2 days. After dried by air at room temperature, the solid culture of each strain obtained herein was pulverized with a mill. The pulverized products were mixed with a clay mineral and a surfactant (Sorpol 5082: manufactured by TOHO Chemical Industry CO., Ltd.), and the cell concentrations of the mixtures were adjusted to $5 \times 10^8$ CFU/g. The obtained mixtures were used as a material for decomposing a plant residue and reducing the volume of the plant residue of Example 2, a material of Comparative Example 3, and a material of Comparative Example 4.

Note that the *Bacillus pumilus* NBRC 12092 strain is a strain registered in NITE Biological Resource Center (NBRC) of National Institute of Technology and Evaluation (2-5-8 Kazusakamatari Kisarazu-shi, Chiba-ken). In addition, the *Bacillus subtilis* BSTH-1 strain is a strain which the inventors of the present invention found out in the upland soil in Chiba and which has a high cellulose-degrading ability.

The strain has been deposited to International Patent Organism Depositary of Advanced Industrial Science and Technology (central 6, 1-1-1 Higashi Tsukuba, Ibaraki) under accession No. FERM P-20663 as of Sep. 13, 2005. Then, the strain was transferred to the international deposition under Budapest Treaty and assigned with accession No. FERM BP-10842 on Jun. 19, 2007.

(3) Decomposition and Volume-Reduction Test of Mowed Turf

The material for decomposing a plant residue and reducing the volume of the plant residue of Example 1, which was obtained as described above, was evaluated for an ability of decomposing a mowed turf or reducing the volume of the mowed turf by using the decomposition test method for mowed *Zoysia tenuifolia Willd* in a golf course. The *Zoysia tenuifolia Willd* in the fairway in a golf course was cut to have a length of 5 to 10 mm and the resultant was dried sufficiently for 10 days in the sun. A predetermined amount (1 g) of the dried products were each put in a flask. 10 ml of water were added to each flask and sterilized with an autoclave. Then, 100 µl ($1\times10^8$ CFU) of each of the material for decomposing a plant residue and reducing the volume of the plant residue of Example 1, the materials of Comparative Examples 1 and 2 were added thereto, followed by being left to stand at 28° C. for 14 days. After 14 days, each of the mowed turf in those flasks was collected with a doubled gauze, and washed gently with water, followed by drying at 70° C. for 24 hours. Then, the residual weight was measured. A rate of the residual weight to a dried weight of the plant residue before addition of the material for decomposing a plant residue and reducing the volume of the plant residue (decomposition rate (%)) was calculated.

Table 1 shows the results.

TABLE 1

| | Name of strain | Decomposition rate (%) |
| --- | --- | --- |
| Example 1 | *Bacillus pumilus* KS-C4 strain | 30.0 |
| Comparative Example 1 | *Bacillus pumilus* NBRC 12092 strain | 7.5 |
| Comparative Example 2 | *Bacillus subtilis* BSTH-1 strain | 4.1 |

As shown in Table 1, the material for decomposing a plant residue and reducing the volume of the plant residue of Example 1 decomposed 30% of the total quantity of the *Zoysia tenuifolia Willd* with the treatment for 14 days. On the other hand, the decomposition rate of the material of Comparative Example 1 was 7.5% and the decomposition rate of the material of Comparative Example 2 was 4.1%. From the foregoing, the KS-C4 strain was proved to have an extremely high ability of decomposing a mowed turf and reducing the volume of the mowed turf compared to the other strains belonging to the same species and the other strains belonging to the same genus.

(4) Decomposition and Volume Reduction Test of Thatch

The material for decomposing a plant residue and reducing the volume of the plant residue of Example 2, which was obtained as described above, was evaluated for an ability of decomposing a thatch and reducing the volume of the thatch. The green (bent green) in a golf course in Chiba was used for the evaluation. The material for decomposing a plant residue and reducing the volume of the plant residue of Example 2 and materials of Comparative Examples 3 and 4 were each diluted with water 1.000-fold and sprayed at 1 g of the material ($5\times10^8$ CFU) per 1 m² of the green. 60 days after the spraying, three samples including a part of the turf cut with a soil cutter at each treatment district were collected and the root part thereof were washed with flowing water. After that, the thickness of a thatch part remaining below the leave and stem of the turf was measured. In addition, an average value of the thickness of the thatch part at each treatment district was calculated. Then, a difference between the treatment district and the non-treatment district was evaluated as a thatch reduction rate (%).

Table 2 shows the results.

TABLE 2

| | Name of strain | Thickness of thatch (mm: average value) | Thatch reduction rate (%) |
| --- | --- | --- | --- |
| Example 2 | *Bacillus pumilus* KS-C4 strain | 28.9 | 23.2 |
| Comparative Example 3 | *Bacillus pumilus* NBRC 12092 strain | 32.4 | 14.1 |
| Comparative Example 4 | *Bacillus subtilis* BSTH-1 strain | 33.6 | 10.8 |
| Non-treatment district | — | 37.7 | — |

As shown in Table 2, in the district treated with the material for decomposing a plant residue and reducing the volume of the plant residue of Example 2, 23.2% of the thickness of the thatch part was confirmed to reduce after 60 days compared to the non-treatment district. On the other hand, the thatch reduction rate in the district treated with the material of Comparative Example 3 was only 14.8% and the thatch reduction rate in the district treated with the material of Comparative Example 4 was only 10.8% 11.1%. From the foregoing, the KS-C4 strain was proved to have an extremely high ability of decomposing a thatch and reducing the volume of the thatch compared to the other strains belonging to the same species and the other strains belonging to the same genus.

(5) Decomposition and Volume Reduction Test of Mowed Grass

The material for decomposing a plant residue and reducing the volume of the plant residue of Example 1, which was obtained as described above, was evaluated for an ability of decomposing a mowed grass and reducing the volume of the mowed grass by a similar method in the item (3). The plant species of the mowed grass used in the evaluation are shown in Table 3. Those plants are derived from exuberant weeds at a river levee or the like. Those mowed grasses were dried sufficiently for 10 days in the sun and then cut to have a length of 5 to 10 mm. A predetermined amount (2 g) of the dried products was put in a flask. 30 ml of water were added to each flask and sterilized with an autoclave. Then, 100 µl ($1\times10^8$ CFU) of the material for decomposing a plant residue and reducing the volume of the plant residue of Example 1 was added thereto, followed by being left to stand at 28° C. for 14 days. After 14 days, the dried weight was measured in the same way as in the item (3), whereby the degree of the decomposition and volume reduction was evaluated.

[Evaluation Criteria]

++: reduction of 50% or more

+: reduction of 20 to 50%

Table 3 shows the results.

TABLE 3

| Name of weeds | Family | Degree of decomposition and volume reduction |
|---|---|---|
| Galium spurium var. echinospermon | Rubiaceae | ++ |
| Pleioblastus chino var. chino | Gramineae | + |
| Dactylis glomerata | Gramineae | + |
| Miscanthus sinensis | Gramineae | + |
| Helianthus tuberosus | Asteraceae | + |
| Artemisia princeps Artemisia | Asteraceae | ++ |
| Equisetum arvense | Equisetaceae | ++ |
| Cirrus of Pueraria lobata | Leguminosae | + |

As shown in Table 3, the KS-C4 strain exhibited high ability of decomposing various weeds and reducing the volume of the various weeds, particularly broad leaf weeds. From the foregoing, it was proved that the material for decomposing a plant residue and reducing the volume of the plant residue of the present invention were able to be used favorably in decomposition and volume reduction of the mowed grass as well.

(6) Decomposition and Volume Reduction Test of Crop Residue

The material for decomposing a plant residue and reducing the volume of the plant residue of Example 2, which was obtained as described above, was evaluated for an ability of decomposing a root residue and reducing the volume of the root residue in the soil after strawberry harvest. The material for decomposing a plant residue and reducing the volume of the plant residue of Example 2 and the material of Comparative Examples 4 were each diluted with water 1.000-fold and sprayed at 5 g of the material ($2.5 \times 10^9$ CFU) per 1 m$^2$ to a strawberry field where a root residue remained after strawberry harvest. 30 days after the spraying, soil in predetermined amounts at three sites in each treatment district was collected and dried by air. Next, the soil dried by air was subjected to a sieve (with a mesh size of 2 mm), and the root residue such as the root or the stem remained on the sieve was collected. Then, the weight of the root residue was measured (residue content). A difference between the treatment district and the non-treatment district was evaluated as a residue reduction rate (%).

Table 4 shows the results.

TABLE 4

| | Name of strain | Residue content (g/100 g soil) | Residue reduction rate (%) |
|---|---|---|---|
| Example 2 | Bacillus pumilus KS-C4 strain | 0.62 | 42.6 |
| Comparative Example 4 | Bacillus subtilis BSTH-1 strain | 0.76 | 29.6 |
| Non-treatment district | — | 1.08 | — |

As shown in Table 4, the district treated with the material for decomposing a plant residue and reducing the volume of the plant residue of Example 2, 42.6% of the root residue was confirmed to reduce after 30 days compared to the non-treatment district. On the other hand, the residue reduction rate in the district treated with the material of Comparative Example 4 was only 29.6%. From the foregoing, the KS-C4 strain was proved to have an extremely high ability of decomposing a crop residue and reducing the volume of the crop residue compared to the other strains belonging to the same genus.

The invention claimed is:

1. An isolated Bacillus pumilus KS-C4 strain (FERM BP-10842) having an ability of decomposing a plant residue and reducing a volume of the plant residue.

2. A material for decomposing a plant residue and reducing a volume of the plant residue, comprising, as an active ingredient, cells of the strain according to claim 1 or a culture of the cells of the strain.

3. A method of decomposing a plant residue and reducing a volume of the plant residue, comprising adding the material for decomposing a plant residue and reducing a volume of the plant residue according to claim 2 to a plant residue.

4. The material according to claim 2, comprising, as an active ingredient, cells of the strain.

5. The material according to claim 2, comprising, as an active ingredient, a culture of the cells of the strain.

6. A method of decomposing a plant residue and reducing a volume of the plant residue, comprising adding the material for decomposing a plant residue and reducing a volume of the plant residue according to claim 4 to a plant residue.

7. A method of decomposing a plant residue and reducing a volume of the plant residue, comprising adding the material for decomposing a plant residue and reducing a volume of the plant residue according to claim 5 to a plant residue.

* * * * *